United States Patent [19]
Jacobsen et al.

[11] Patent Number: 5,618,269
[45] Date of Patent: Apr. 8, 1997

[54] PRESSURE-DRIVEN ATTACHABLE TOPICAL FLUID DELIVERY SYSTEM

[75] Inventors: Stephen C. Jacobsen; Clark C. Davis; Kent Backman, all of Salt Lake City, Utah

[73] Assignee: Sarcos, Inc., Salt Lake City, Utah

[21] Appl. No.: 435,092

[22] Filed: May 4, 1995

[51] Int. Cl.$^6$ ................................................ A61M 7/00
[52] U.S. Cl. ...................... 604/118; 604/131; 604/141; 604/152; 604/153; 417/395
[58] Field of Search ................................ 604/4, 30, 31, 604/33, 65, 66, 67, 80, 81, 93, 118, 131, 132, 151, 152, 153; 222/243, 275, 409, 630, 206, 207, 209, 212, 213, 214, 215; 417/378, 391, 395

[56] References Cited

U.S. PATENT DOCUMENTS

| | | | |
|---|---|---|---|
| 247,360 | 9/1881 | Jay | 92/168 |
| 2,750,746 | 6/1956 | Brannen | 60/54.6 |
| 2,766,701 | 10/1956 | Giraudeau | 103/153 |
| 3,019,739 | 2/1962 | Prosser | 103/204 |
| 3,509,890 | 5/1970 | Phillips | 134/122 |
| 3,742,822 | 7/1973 | Talbert | 92/86 |
| 4,042,248 | 8/1977 | Williamitis | 277/138 |
| 4,280,741 | 7/1981 | Stoll | 308/3.5 |
| 4,299,220 | 11/1981 | Dorman | 128/260 |
| 4,384,511 | 5/1983 | Mefferd | 92/164 |
| 4,437,821 | 3/1984 | Ogawa | 418/104 |
| 4,637,295 | 1/1987 | Powers et al. | 92/170 |
| 4,662,829 | 5/1987 | Nehring | 417/395 |

*Primary Examiner*—Sam Rimell
*Assistant Examiner*—Robert V. Racunas
*Attorney, Agent, or Firm*—Thorpe North & Western, L.L.P.

[57] ABSTRACT

A fluid delivery device for delivering fluid from a fluid reservoir to a patient. The device includes an inlet channel in communication with a fluid reservoir and a dosing chamber, and an outlet channel disposed in communication with the dosing chamber. A reciprocating dosing actuator is moveable in a reciprocating motion between first and second positions for alternately (i) transporting a dose of fluid conveyed by the inlet channel into the intermediate dosing chamber, and (ii) ejecting the dose from the dosing chamber through the outlet channel to the patient, respectively.

16 Claims, 7 Drawing Sheets

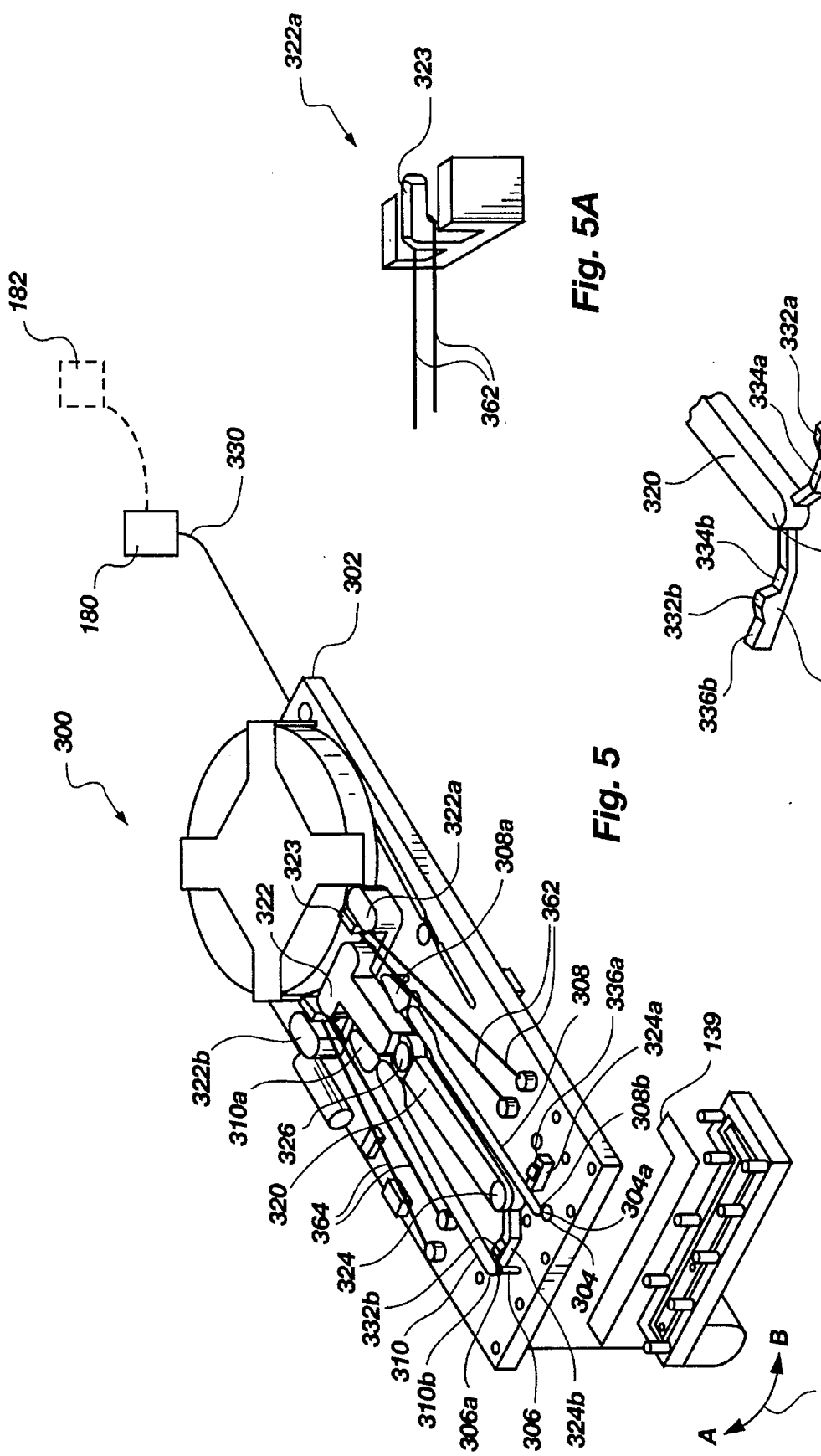
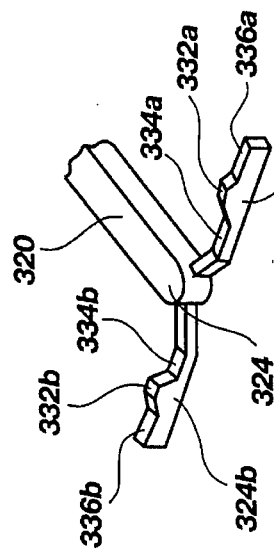
Fig. 5A
Fig. 5B
Fig. 5

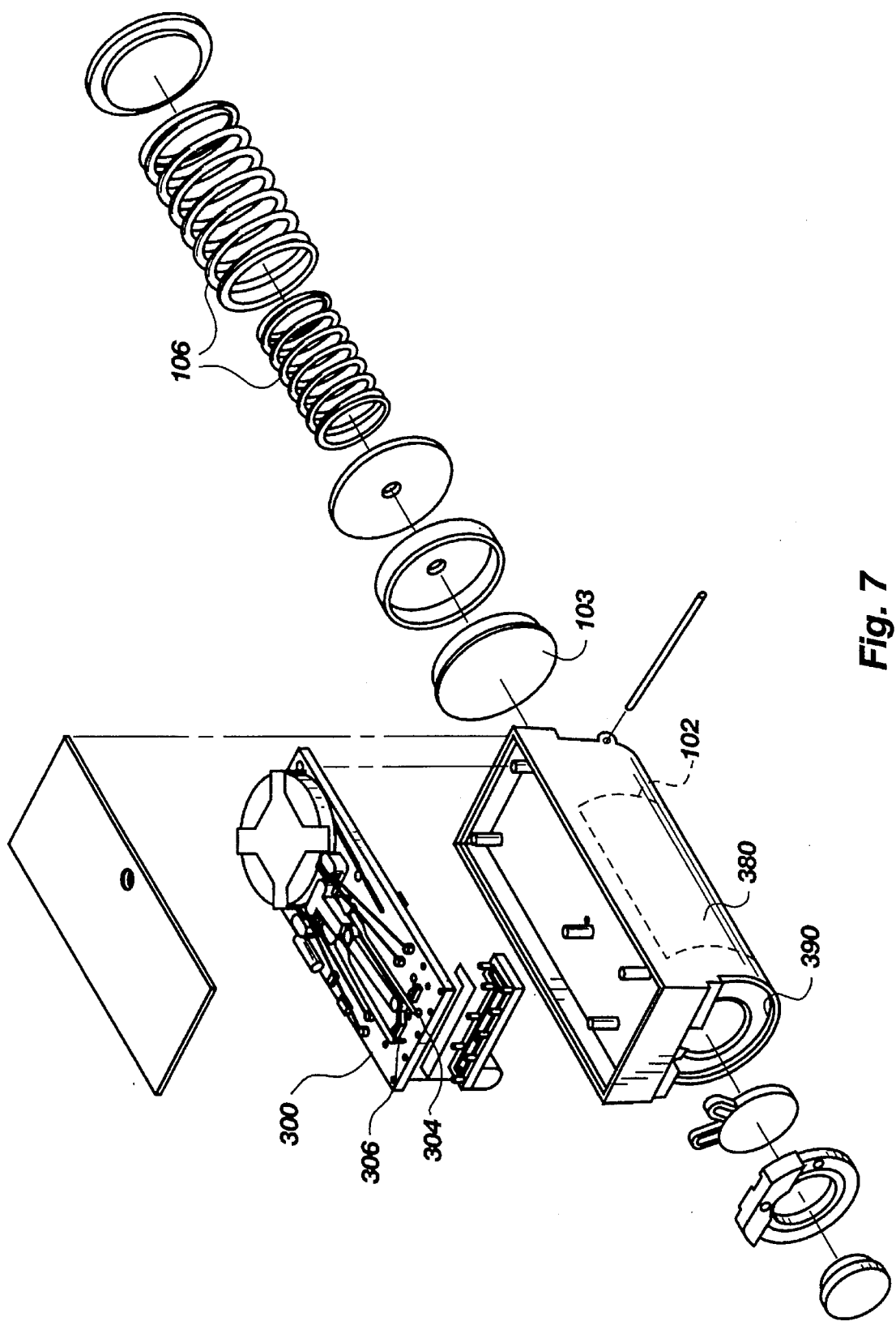

PRESSURE-DRIVEN ATTACHABLE TOPICAL FLUID DELIVERY SYSTEM

BACKGROUND OF THE INVENTION

1. The Field of the Invention

The present invention relates generally to fluid delivery systems, and more particularly to lightweight, miniaturized fluid transport systems suitable for a variety of uses including topical and intravenous fluid delivery.

2. The Background Art

The administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently involves the standard syringe and needle. This simple method is not conducive to a progressive and systematic delivery of multiple doses of fluid over a longer time period. It is known to meet such needs with the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

The disposable non-electric pumps generally consist of small elastomeric bags within a hard shell container, in which the bags are filled with IV solution under pressure. The pressure generated by the contraction of the elastomeric bag forces the IV solution through a fixed orifice at a constant flow rate into the patient's vein. Although these pumps are much less expensive than the electronic pumps and eliminate the need for maintenance (since they are discarded after every use), their drawbacks include the lack of monitoring capability, the lack of the ability to select different flow rates, limited fluid capacity, and still relatively high cost for a disposable product.

It is often desirable to accomplish fluid delivery by a topical administration of the fluid to allow the fluid to drift into the skin by osmosis. The HARTS COLLAR™ is known in the art to include a porous fluid holder for strapping around the neck of a patient, usually a dog. The porosity of the collar is designed to release the contained fluid from the collar at a desirable rate onto the skin of the patient to enable the skin to gradually absorb the fluid. The drawbacks include nonuniform application due to movement of the patient, nonuniform delivery rates, and the lack of ability to select different flow rates.

OBJECTS AND SUMMARY OF THE INVENTION

It is therefore an object of the present invention to provide a fluid delivery system which is especially suitable for use in topical administration of fluids to a patient, either human or animal.

It is a further object of the invention to provide such a fluid delivery system which is easy to manufacture and which utilizes low cost parts.

It is an additional object of the invention to provide such a fluid delivery system which is efficient and reliable.

It is another object of the invention, in accordance with one aspect thereof, to provide such a fluid delivery system having a readily changeable flow rate.

It is yet another object of the invention, in accordance with one aspect thereof, to provide such a fluid delivery system which is portable and miniaturized so as to be carryable by the patient.

It is an additional object of the invention, in accordance with one aspect thereof, to provide such a fluid delivery system which delivers doses of fluid to the patient according to a timed sequence.

The above objects and others not specifically recited are realized in a specific illustrative embodiment of pumping apparatus in combination with valved guide channels. A housing includes first and second intersecting side walls defining a concavo-convex lens-shaped cavity. The cavity is divided into first and second sealed sections by a resilient membrane which is sealably attached in an expanded configuration about its entire perimeter along an intersection of the first and second side walls. A first guide channel fluidly connects a fluid supply reservoir to the first section of the cavity, and a second guide channel fluidly connects the first guide channel to the second section of the cavity. An outlet channel also communicates with the second section. First and second active valves are disposed in the first and second guide channels, respectively, for blocking and releasing fluid flow within the channels. A propellant, such as a pressurized spring apparatus or other suitable propellant, is disposed in the fluid supply reservoir and provides the driving force for the system.

When the first valve is opened and the second valve is closed, positive pressure exerted by the propellant forces fluid from the reservoir into the first section of the cavity and expands the membrane into a diastolic position. When the first valve is closed the membrane is shielded from the influence of the propellant pressure, and when the second valve is then opened, the elastic memory of the membrane causes it to contract to a systolic position and force fluid from the first section of the cavity through the second guide channel and into the second section of the cavity. It will thus be appreciated that when the propellant is allowed to force fluid into the first section of the cavity, the resulting diastolic expansion of the membrane causes the membrane to expand into the second section of the cavity and eject a previous dose of fluid residing in the second section out through the outlet channel.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 5 is a perspective view of a switching device made in accordance with the principles of the present invention;

FIG. 5A shows an enlarged view of a first end portion of a shaft body of the switching device of FIG. 5;

FIG. 5B shows an enlarged, fragmented view of a second end of the shaft body of the switching device of FIG. 5;

FIG. 7 is an exploded perspective view of a portion of the fluid delivery pump of FIG. 3A in combination with a switching device.

DETAILED DESCRIPTION

Figure 1:
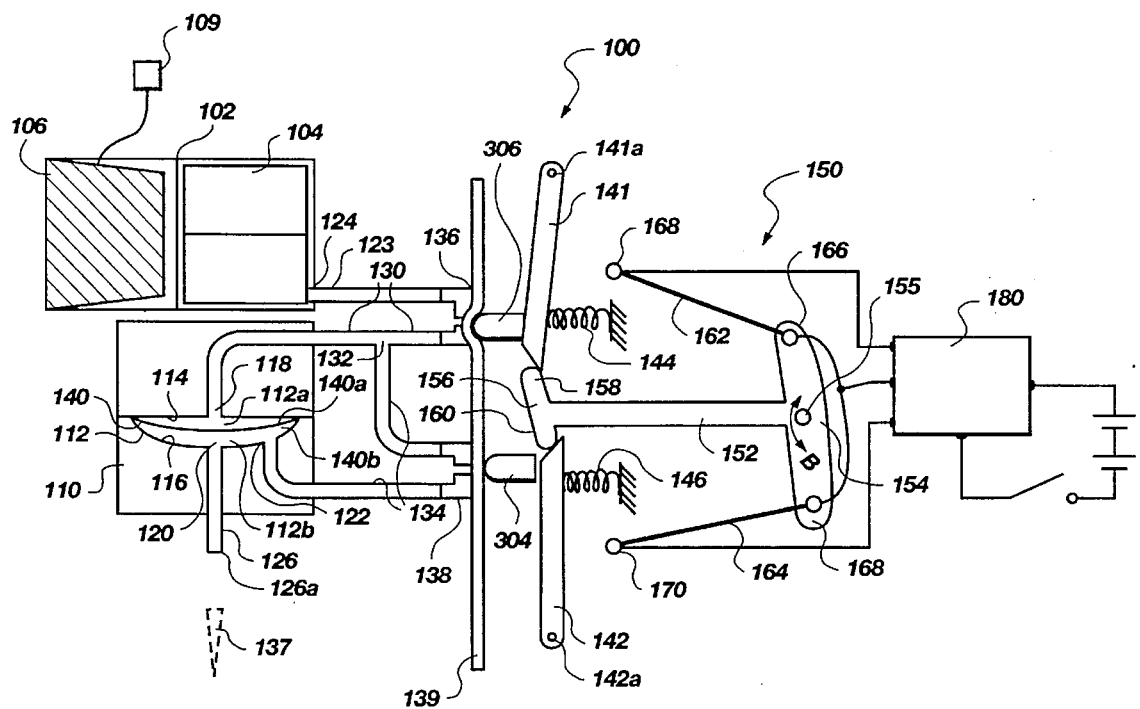
FIG. 1 is a schematic illustration of a propellant-actuated fluid delivery pump made in accordance with the principles of the present invention.

FIGS. 1–3 illustrate the features of a propellant-actuated fluid delivery device, generally designated at 100. The device 100 includes a fluid reservoir 102 for containing a supply of fluid 104 to be delivered to a patient. A propellant 106 is disposed in the reservoir 102 for exerting a continuous positive pressure within the reservoir. The propellant 106 may comprise any suitable pressure means for exerting a positive pressure within the reservoir 102, such as a pressurized spring-loaded member or a gas spring.

A housing 110 includes an intermediate dosing chamber 112 formed therein. The dosing chamber 112 preferably comprises a lens-shaped concavo-convex chamber including a first interior side wall 114 and an opposing second interior side wall 116. The first interior side wall 114 is preferably convex, while the second interior side walls 116 is preferably concave. An inlet port 118 is formed in the first interior side wall 114. An outlet port 120 and an intermediate port 122 are formed in the second interior side wall 116.

An inlet channel 123 is disposed in fluid communication at 124 with the fluid-containing portion of the reservoir 102, and an outlet channel 126 is disposed in fluid communication with the dosing chamber 112 via the outlet port 120. The outlet channel 126 includes a distal end or discharge end 126a. A first guide channel 130 fluidly connects the inlet channel 123 with the inlet port 118, and includes a diversion port 132 formed therein. A second guide channel 134 fluidly connects the diversion port 132 of the first guide channel 130 with the intermediate port 122 of the second interior side wall 116 of the dosing chamber 112. A first active valve 136 is disposed in the first guide channel 130 at a location between the inlet channel 123 and the diversion port 132, for alternately blocking and releasing fluid flow within the first guide channel 130 when maneuvered into closed and opened positions, respectively. A second active valve 138 is disposed in the second guide channel 134 at a location between the diversion port 132 and the intermediate port 122 for alternately blocking and releasing fluid flow within the second guide channel 134 when maneuvered into closed and opened positions, respectively.

The first and second valves 136 and 138 are preferably active valves as known in the art which must be actively opened and closed for operation. The valves 138 and 136 are most preferably pinch valves including first and second pinch pins 304 and 306, respectively. The pinch pins 304 and 306 rest against a resilient membrane 139 which deforms into the fluid channels and blocks flow when the pins are forced into the membrane. When a pin 304 is pulled in a direction away from the membrane 139, elastic memory operates to contract the membrane 139 back into a natural position and release fluid flow within the fluid channel. Levers 141 and 142 and associated springs 144 and 146 bias the pinch pins 304 and 306, respectively, in the absence of a competing force. If some other force pulls a lever 141 or 142 away from the membrane 139, the lever will pivot about its pivot point 141a or 142a to release the membrane from blocking the flow. FIG. 1 shows the first valve 136 in a closed position and the second valve 138 in an open position.

A resilient membrane 140 is sealably attached in an expanded configuration along a circumferential portion thereof to the interior walls of the dosing chamber 112, preferably to an intersection of the first and second interior side walls 114 and 116, said intersection forming an intermediate circumferential section of the dosing chamber. The membrane 140 thus divides the dosing chamber 112 into first and second sections 112a and 112b, respectively. The membrane 140 includes first and second opposing sides 140a and 140b, respectively, the first side 140a facing the inlet port 118 and the second side 140b facing the outlet port 120 and the intermediate port 122. The attachment of the membrane 140 in an expanded configuration enables elastic memory of the molecular structure of the membrane acts to contract the membrane toward the inlet port 118. The membrane 140 is preferably attached such that it contiguously contacts and rests against the first interior side wall 114 before reaching its natural contracted state. The membrane 140 is alternately expandable toward the outlet port 120 to a diastolic position and contractible toward the inlet port 118 to a systolic position as explained below in more detail.

The terms "diastole", "systole" and their various grammatic forms are used herein to refer by analogy to the rhythmic dilation and contraction of the heart. Thus, the chamber 112 fills during the diastolic expansion phase of the membrane 140, and is purged when the membrane systolically contracts against the first interior side wall 114. However, the "back" or second section 112b of the chamber 112 fills at the same time the membrane 140 forces fluid out of the first section 112a. The membrane 140 is thus continuously expanding and contracting to alternately accept fluid against its first side 140a and force fluid through the second guide channel 134 to its opposing second side 140b.

A suitable driving mechanism, generally designated at 150, includes a shaft means 152 having first and second opposing T-sections 154 and 156. The shaft means 152 is pivotally attached at a pivot point 155. Shape memory wires 162 and 164 are attached at their ends to opposing ends 166 and 168 of the first T-section 154 of the shaft means 152. The wires 162 and 164 are anchored at 168 and 170 at their opposing ends. Opposing ends 158 and 160 of the second T-section 156 are disposed adjacent to free ends of the levers 141 and 142, respectively.

In operation, the shape memory wires 162 and 164 are caused to contract alternately so as to pivot the shaft means 152 back and forth between first and second positions about the pivot point 155, in the directions of arrow B. Pivotal movement of the shaft means 152 causes ends 158 and 160 of the second end 156 to alternately force the levers 141 and 142 in a direction outwardly away from the membrane 139. This permits the valve pins 306 and 304 to retract in a direction away from the membrane 139 to thereby release fluid flow in the first and second guide channels 130 and 134, respectively. It will be appreciated that when the propellant 106 operates to exert a continuous positive pressure within the reservoir 102, the fluid 104 is caused to flow into the inlet channel 123. Fluid flow into the first and second guide channels 130 and 134 can thus be controlled by manipulation of the first and second valves 136 and 138, which are in turn controlled by the shape memory wires 162 and 164, respectively.

When the first valve 136 is opened and the second valve 138 is closed, positive pressure exerted by the propellant 106 forces the fluid 104 from the reservoir 102 through the inlet channel 123 and first guide channel 130 into the first section 112A of the dosing chamber 112 and expands the membrane 140 into a diastolic position to fill the chamber. Preferably, the membrane contacts the second interior side wall 116 when in the expanded diastolic position. When the first valve 136 is closed the membrane 140 is shielded from the influence of the propellant pressure. When the second valve 138 is then opened, the elastic memory of the membrane 140 causes it to contract to a systolic position and force fluid from the first section 112a of the chamber 112 back through the inlet port 118. The fluid then passes through the diversion port 132, through the second guide channel 134, and through the intermediate port 122 into the second section 112b of the chamber 112. It will thus be appreciated that when the propellant 106 is allowed to force fluid into the first section 112a of the chamber 112, the resulting diastolic expansion of the membrane 140 causes the membrane to expand into the second section 112b of the chamber 112 and eject a previous dose of fluid residing in the second section out through the outlet channel 126.

An important feature of the driving mechanism 150 is that the shaft means 152 and levers 141 and 142 are designed such that when the shaft means resides in a center position between first and second pivoted positions, both valves 136 and 138 are closed. Put another way, there is no position wherein both of the valves 136 and 138 are open. This is important for proper dosing operation.

Figure 2A:
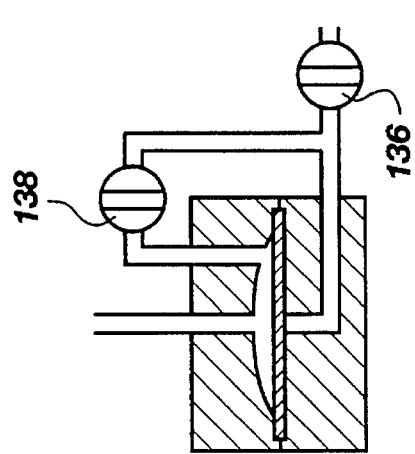
FIGS. 2A–D are fragmented, schematic illustrations of valved guide channels in the fluid delivery pump of FIG. 1, in various open and closed configurations.
Figure 2B:
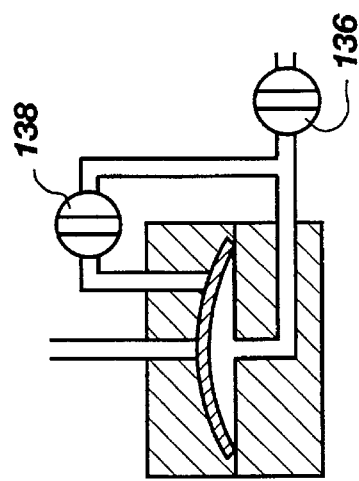
Figure 2C:
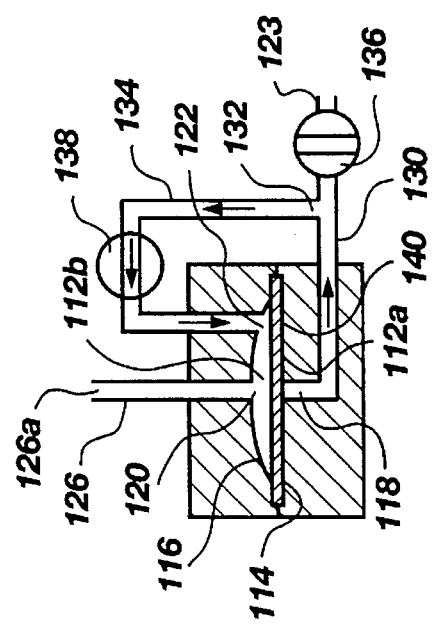
Figure 2D:
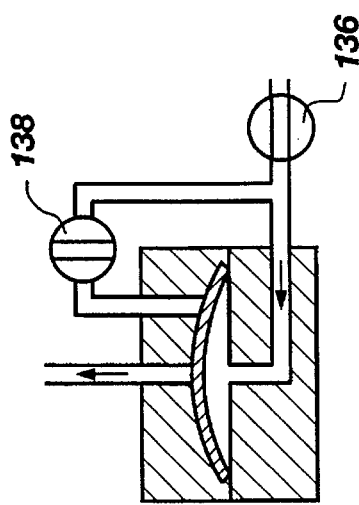

The dosing action discussed above is further illustrated in FIGS. 2A–D, which respectively represent four main steps in the dosing cycle. Representative reference numerals are provided in FIG. 2A and should be read to apply also to FIGS. 2B–D. FIG. 2A shows the first valve 136 in a closed position and the second valve 138 in an opened position. This configuration shields the membrane 140 from pressure exerted by the propellant 106 (not shown in FIGS. 2A–D) and permits the membrane to contract against the first interior side wall 114. Contraction of the membrane 140 forces fluid residing in the first section 112a of the chamber 112 through the second valve 138 and through the intermediate port 122 to fill the second section 112b of the chamber. FIG. 2B shows the first valve 136 in a closed position and the second valve 138 in a closed position. FIG. 2C shows the first valve 136 in an opened position and the second valve 138 in a closed position. The configuration of FIG. 2C permits pressure exerted by the propellant to force another dose of fluid into the dosing chamber 112 to thereby expand the membrane 140 toward the outlet and intermediate ports 120 and 122, causing the membrane 140 for forcibly eject the previous dose from the second section 112b out through the outlet channel 126. The size of the dosing chamber 112 determines the dosage size ejected. FIG. 2D shows the first valve 136 in an closed position and the second valve 138 in a closed position, ready again for the step shown in FIG. 2A.

It was noted above that the membrane 140 is sealed along a circumferential portion thereof to the interior walls of the dosing chamber 112, preferably to an intersection of the first and second interior side walls 114 and 116. Most preferably, the membrane 140 is continuously sealed along its outer perimeter edge such that the first and second sections 112a–b of the dosing chamber 112 are sealed by the membrane. However, alternatively configurations are within the scope of the present invention, and the phrase "circumferential portion" as used herein with respect to the membrane 140 shall not be limited in meaning to the perimeter edge but shall also include some interior circular portion of the membrane. The membrane 140 also need not be continuously sealed along any such circumferential portion, although such is preferred.

It is also preferred, but not required, that the membrane 140 contract against the first interior side wall 114 so as to minimize dead space within the dosing chamber 112. However, the membrane 140 need not contact the first interior side wall 114 for operation of the device 100.

The device 100 may include a suitable pressure-varying means 109 connected to the propellant 106 to selectively vary the magnitude of the pressure exerted thereby. Such pressure-varying means 109 can be operated to vary the rate of transport of the fluid 104 to and from the dosing chamber 112.

The distal end 126a of the outlet channel 126 delivers the fluid pumped from the reservoir 102. The distal end 126a is placed proximate to the desired point of delivery of the fluid. If topical delivery is desired, the distal end 126a may be placed against a portion of the skin which is to absorb the fluid. Alternatively, an intravenous needle 137 (shown in phantom line in FIG. 2) may be attached to the distal end 126b for intravenous application of the fluid pumped from the reservoir 102. It will be appreciated that many alternative methods of fluid delivery can be used with applicants' fluid delivery device 100.

Figure 3B:
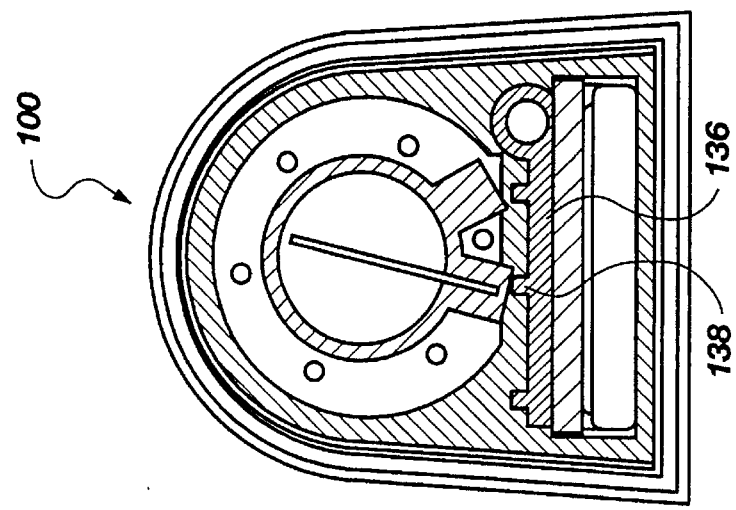
FIG. 3B is an end cross-sectional view of the fluid delivery pump of FIG. 3A.
Figure 3A:
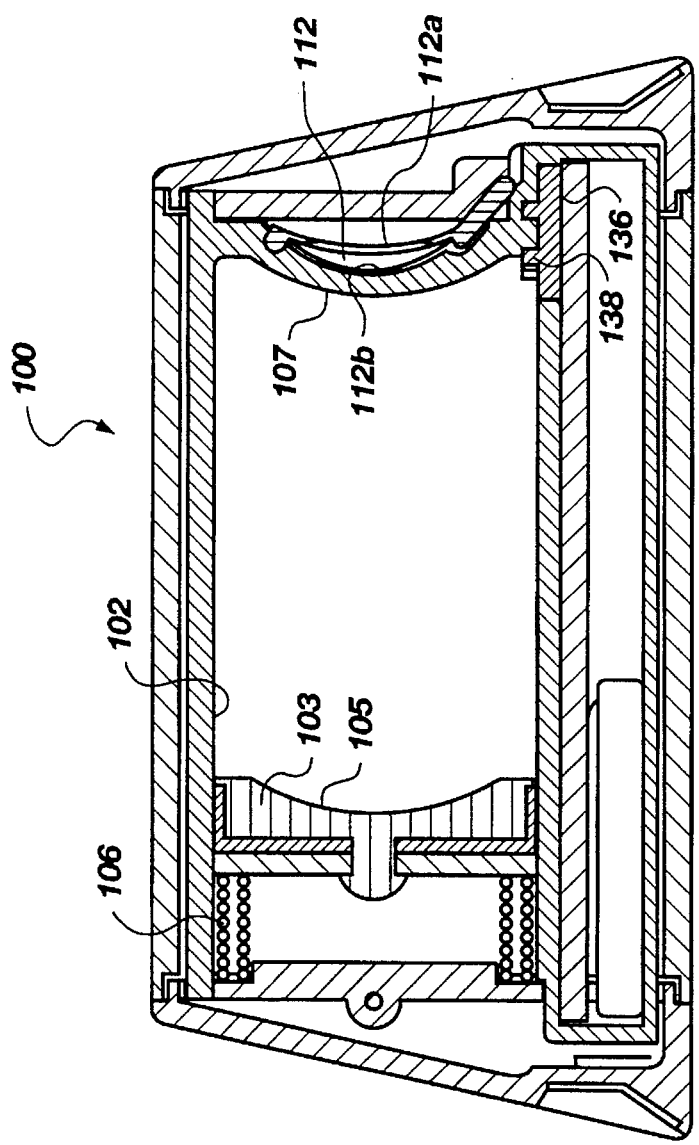
FIG. 3A is a side, cross-sectional view of a preferred embodiment of the fluid delivery pump of FIG. 1.

FIGS. 3A–B show more detailed views of the reservoir 102 and propellant 106. The propellant includes a ram 103 having a concave-shaped surface 105 corresponding to an opposing convex-shaped surface 107 of the reservoir 102. As fluid is pumped from the reservoir 102, the ram 103 is propelled toward the convex-shaped surface 107 by the propellant 106. The ram 103 eventually comes to rest against the convex-shaped surface 107, such that the corresponding concave and convex surfaces 105 and 107 enable substantially all of the fluid to be propelled from the reservoir 102 to thereby minimize dead space within the reservoir 102.

Figure 4:
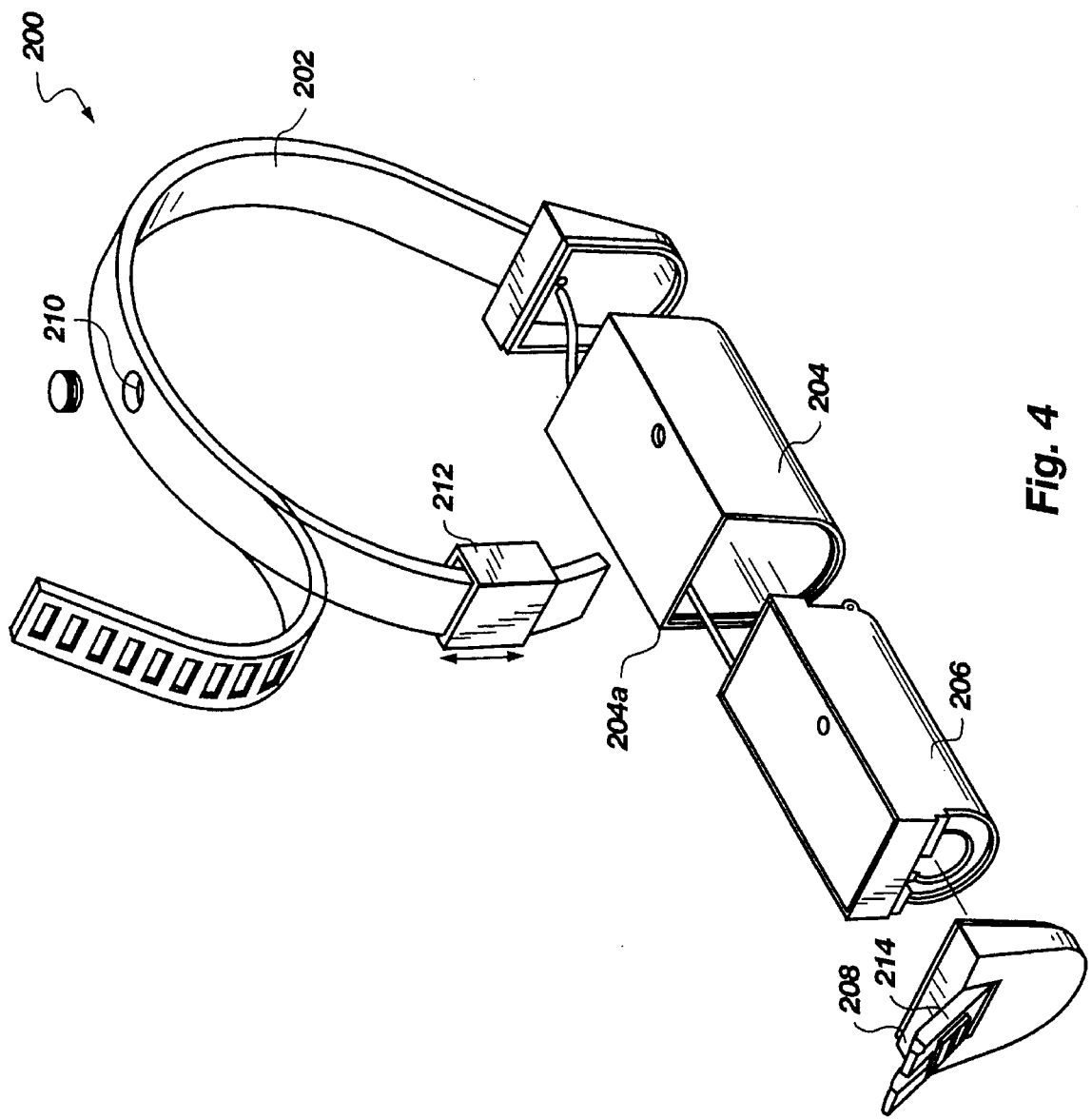
FIG. 4 is an exploded, perspective view of attachment and containment structure made in accordance with the principles of the present invention.

One advantage of the present invention is portability. It will be appreciated by those skilled in the art that the device 100 may be readily constructed from lightweight materials in relatively small dimension. Referring now to FIG. 4, one application envisioned for the present invention is to incorporate the fluid device 100 into a collar device generally designated at 200. The collar device 200 can be strapped around the neck of a dog to deliver doses of fluid at a desired rate, such as anti-tick solution, anti-flea solution, anti-heartworm solution, and so forth. Accordingly, the term "patient" as used herein with respect to application of the invention shall refer broadly to both humans and animals.

The collar device 200 includes a strap 202 for attachment around a patient's neck. A casing 204 receivably contains a pumping device 206 (corresponding to the device 100 of FIG. 1), which is held in place by an end cap 208 which is welded onto an end 204 of the casing 204. An outlet tube 204 (corresponding to 126 in FIG. 1) runs from the pump 206 through one side of the collar 202 and discharges through a cavity 210 formed in the collar 202 onto the back of the patient's neck. A slidable lock 212 locks onto a locking tab 214 in any suitable fashion to secure the collar 202 onto the patient's neck. The collar device 200 enables attachment of the pump 206 to the patient to thereby enable the pump to be carried by the patient in a convenient manner, such that movement of the pump 206 is confined to movement with the patient.

In another application envisioned for the invention, the device 100 of FIG. 1 is dimensioned and sized so as to be swallowable by the patient to thereby enable the pump to deliver fluid within an intracorporeal region of the patient. For example, a pump in accordance with the invention could contain a supply of anti-parasitic solution useful to prevent parasites on cows. After the cow swallows the miniature pump, it comes to reside in the cow's rumen (the first of the cow's stomachs) and delivers the solution directly into the cow where the solution is advantageously absorbed by the cow. Thus, the phrase "configured for attachment to the patient" as used herein with respect to the invention shall refer broadly to a pumping device which can be strapped to a part of a patient, and/or which can be swallowed by the patient.

It will be appreciated that the invention may include a control means 180 electrically connected to the driving mechanism 150 (in FIG. 1). The control means may include a timer as known in the art for producing timing signals. It will be appreciated that the driving mechanism can be designed to be activated and/or deactivated responsive to the timing signals produced by the timer of the control means. The control means could alternatively include sensing means responsive to some physiological condition of the patient. When the physiological condition of the patient, such as the patient's temperature, reaches a predetermined level, the sensing means would produce an actuation signal to cause the control means to activate and/or deactivate the driving mechanism. The phrase "physiological condition" as used herein shall refer broadly to any function or activity of living organisms and their parts.

Figure 6:
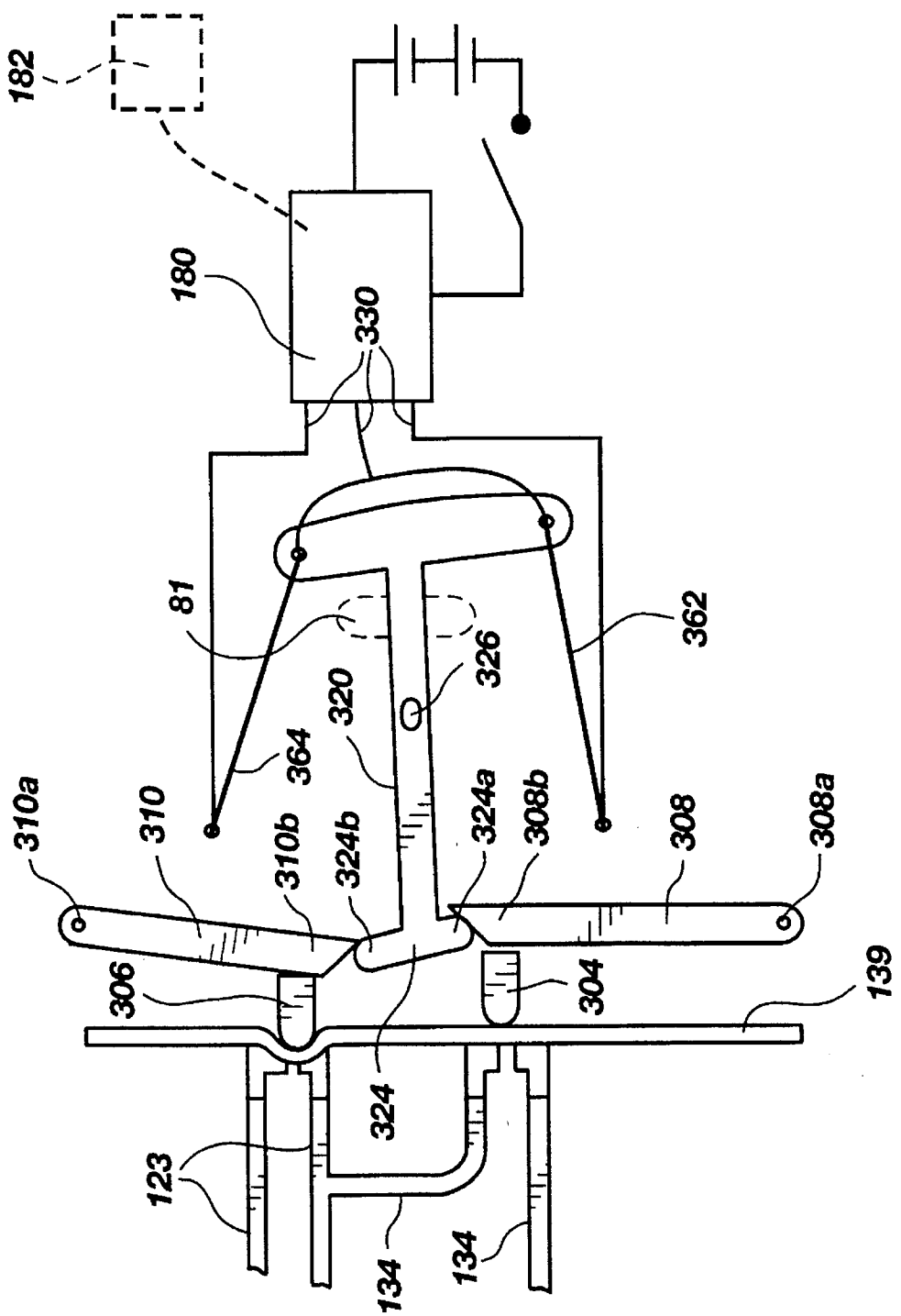
FIG. 6 is a schematic view of the switching device of FIG. 5 as applied to pinch valves.

Referring to FIGS. 5–6, a shape-memory wired switching device 300 is shown. First shape memory wire 362 and second shape memory wire 364 operate to drive the switching device 300, as explained below in more detail. Shape memory materials are malleable when their temperature is below the material's transition temperature. When heated above the transition temperature, the material forcefully returns to its original shape. One method of heating a wire is to pass electric current through it.

The switching device 300 includes a support plate 302. First and second valve pins 304 and 306 each include a proximal end 304a and 306a, and an opposing distal end (not shown). The first and second valve pins 304 and 306 are slidably disposed in the support plate 302 with their distal ends residing against flow channel apparatus such as a resilient membrane 139.

First and second levers 308 and 310 are respectively attached at first portions 308a and 310a thereof to the support plate 302. The levers 308 and 310 are respectively biased at second opposing portions 308b and 310b thereof against the proximal ends 304a and 306a of the first and second valve pins 304 and 306. The levers 308 and 310 thereby exert pressure upon the valve pins 304 and 306, respectively, to force said valve pins into contact with the resilient membrane 139.

A rigid shaft body 320 includes first and second opposing ends 322 and 324, and is pivotally mounted to the support plate 302 at a pivot point 326 thereof. The first opposing end 322 has first and second opposing sides 322a and 322b. The second opposing end 324 includes first and second rod members 324a and 324b extending laterally outward in opposing directions from the shaft body 320.

The first shape memory wire 362 is secured at one end thereof to the support plate 302 and attached at an opposing end thereof to the first side 322a of the first end 322 of the shaft body 320. The second shape memory wire 364 is secured at one end thereof to the support plate 302 and attached at an opposing end thereof to the second side 322b of the first end of the shaft body. As shown most clearly in FIG. 5A, each shape wire is preferably looped around a finger formed on a side of the first end 322 of the shaft body 320. For example, the first shape wire 362 is wrapped around a finger 323 of the first side 322a for a secure attachment thereto. The term "attachment" as used herein with respect to shape memory wires shall thus refer broadly to stationary attachment and looped attachment, as well as any other suitable attachment.

Current means 330 for alternately passing electrical current through the first and second shape memory wires 362 and 364 is electrically connected to said shape memory wires. The current means 330 is electrically connected to a source of electricity 180. The current means 330 is operable in any manner known in the art to alternately cause the first shape memory wire 362 and the second shape memory wire 364 to contract in alternating tandem. Contraction of the first shape memory wire 362 causes the shaft body 320 to pivot about its pivot point 326 in one pivotal direction A shown by arrow 340, and contraction of the second shape memory wire 364 causes the shaft body to pivot about the pivot point in a second pivotal direction B, such that (i) contraction of the first shape memory wire 362 and the resulting pivotal movement of the shaft body 320 causes the first rod member 324a to move between the support plate 302 and the first lever 308 to thereby force the second portion 308b of said first lever in a direction away from the first valve pin 304 to thereby release pressure exerted by the first lever 308 upon its valve pin 304, and (ii) contraction of the second shape memory wire 364 and the resulting pivotal movement of the shaft body 320 causes the second rod member 324b to move between the support plate 302 and the second lever 310 to thereby force the second portion 310b of said second lever in a direction away from the second valve pin 306 to thereby release pressure exerted by the second lever 310 upon its valve pin 306.

It will be appreciated by inspection of FIG. 6 that the alternating contraction and release of the first and second shape memory wires 362 and 364 operate to move the valve pins 304 and 306 toward and away from flow channel structure such as the resilient membrane 139.

It can thus be seen in the illustration of FIG. 5 that the second shape memory wire 364 has been electrically heated to contract. The shaft body 320 has been pivoted in direction B of arrow 340 to force a thicker portion 336b of the second rod member 324b contactably between the support plate 302 and the second portion 310b of the second lever 310 to thereby lift said second portion upward and release the second valve pin 306. At the same time, the first rod member 324a has been moved so that the second portion 308b of the first lever 308 resides above a narrower part 334a of said first rod member, thereby allowing the first lever 308 to force the first valve pin 304 into the support plate 302.

The levers 308 and 310 are thus naturally biased to force the valve pins 304 and 306 into the support plate 302, and operate to pull the pins out of the support plate when a thicker part of the rod members 324a and 324b move between the levers and the support plate. The valve pins can be provided with their own spring-action resistance which biases them partially out of the support plate 302 in the absence of counteracting resistance from the levers. Alternatively, the valve pins can be secured directly to their corresponding levers to move in tandem therewith.

It is preferred to provide the shaft body 320 with the narrower portions 334a–b and thicker portions 336a–b as shown most clearly in FIG. 5B. Bumps 332a–b are provided to prevent vibrations, jarring and other forces from inadvertently pivoting the rod 320 into an undesired switched position. However, it is to be understood that the shaft body 320 can embody numerous varying designs and dimensions of thicker/narrow configurations in order to accomplish the alternating forcing and releasing of the levers 308 and 310. Undesired pivot action of the shaft body 320 can be inhibited further if the pivot point 326 is made to substantially coincide with the center of mass of the shaft body 320 about its pivot point 326 to avoid assisting vibrational or jarring forces in causing undesired pivot action.

The switching device 300 can be used in many applications. For example, the valve pins 304 and 306 can function as part of pinch valve structure as illustrated schematically in FIG. 6. The pins 304 and 306 rest against a resilient membrane 139 and operate to force the membrane to deform into fluid channels 123 and 134 to block fluid flow therein. When a pin 304 or 306 is moved in a direction away from the membrane 139, elastic memory operates to contract the membrane 139 back into a natural position and release fluid flow within the fluid channel.

Referring still to FIG. 6, those skilled in the art will appreciate numerous alternative arrangements for retractably forcing the valve pins 304 and 306 into the membrane 139. For example, the valve pins 304 and 306 can be biased into a natural resting position against the membrane 139 without forcing the membrane into the fluid channel as illustrated by valve pin 304. A pin's associated lever forces the pin into the membrane to cause the membrane to block fluid flow within its adjacent flow channel, as illustrated by valve pin 306 and lever 310. The switching device 300 operates to alternately force and release the valve pins into the membrane to thereby cause the valve pins 304 and 306 to alternately block and release fluid flow within the flow channels 134 and 123, respectively.

It will be appreciated that the switching device 300 has numerous uses and advantages, and the invention is thus not limited to applications involving pinch valves. The reciprocating pivotal movement of the shaft body 320 has independent utility, and can be applied to mobilize a pair of switching means in alternating tandem between first and second switched positions. The device 300 can be designed such that a second valve means (for example valve pin 306 as associated with the membrane 139) is not opened until after a first valve means (for example valve pin 304 as associated with the membrane 139) has been closed, and vice versa, such that there is no position whereby both valve means are open at the same time.

From the foregoing description, it will be appreciated that the switching device 300 of FIGS. 5–6 can be utilized with the fluid delivery device 100 of FIGS. 1–4. It may be desirable to vary the switching rate of the switching device 300. Electronic control means 182 could be electrically connected to the electricity source 180, to control the flow of electricity therefrom, for example by intermittently stopping and releasing electron flow from the electricity source 180.

FIG. 7 shows an exploded perspective view of a preferred embodiment for combining the switching device 300 of FIGS. 5–6 with the pump 100 of FIGS. 1–4. A casing 380 contains the reservoir 102, ram 103 and propellant springs 106. The dosing chamber 112 and accompanying membrane 140 (FIGS. 1–4) are contained in an end 390 of the casing 380, such that the valves 136 and 138 can be disposed in adjacent relation with the valve pins 304 and 306 of the switching device 300.

Those skilled in the art will appreciate that the scope of the present invention encompasses many combinations and a broad spectrum of features and structures equivalent to those specifically discussed herein. The principles of the invention may thus be used in any setting requiring the advantages thereof. Those having ordinary skill in the field of this invention will appreciate the advantages of the invention and its application to a wide variety of uses. The present invention represents a significant advance in the field of fluid delivery. Those skilled in the art will appreciate from the preceding disclosure that the objectives stated above are advantageously achieved by the present invention. It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A fluid delivery device for delivering fluid to a patient comprising:

a reservoir for containing a supply of the fluid;

an inlet channel disposed in fluid communication with the reservoir;

an outlet channel disposed in series and in fluid communication with the inlet channel such that said inlet channel resides between the reservoir and the outlet channel;

pressure means disposed on the reservoir for exerting a continuous positive pressure within said reservoir;

a housing having interior walls including first and second interior side walls defining an intermediate dosing chamber, said first side wall having an inlet port formed therein and said second side wall having an outlet port and an intermediate port formed therein, the inlet and outlet channels being disposed in communication with the dosing chamber via the inlet port and the outlet port, respectively;

a resilient membrane sealably attached in an expanded configuration along a circumferential portion thereof to the interior walls of the housing to divide the dosing chamber into first and second sections, said membrane having a first side facing the inlet port to define the first section and an opposing second side facing the outlet port and the intermediate port to define the second section, such that elastic memory of the molecular structure of the membrane acts to contract the membrane toward the inlet port, said membrane being alternately expandable toward the outlet port to a diastolic position and contractible toward the inlet port to a systolic position;

guide channel means disposed in communication with the inlet channel, inlet port and intermediate port for channeling fluid between the inlet channel and the inlet port, and between the inlet port and the intermediate port;

dosing actuation means disposed on the guide channel means including a reciprocating portion being movable in a reciprocating motion between second and first positions for respectively (i) releasing fluid flow between the inlet channel and the inlet port while blocking fluid flow between the inlet port and the intermediate port to permit pressure exerted by the pressure means to force a dose of fluid from the reservoir into the first section of the dosing chamber and against the membrane to forcibly expand the membrane into a diastolic position, and (ii) releasing fluid flow between the inlet port and the intermediate port while blocking fluid flow between the inlet channel and the inlet port to thereby shield the membrane from pressure exerted by the pressure means and permit the elastic memory of the membrane to contractably move the membrane toward the inlet port to a systolic position to force the dose of fluid out of the first section of the dosing chamber back through the inlet port toward the intermediate port to thereby force a dose of fluid through the intermediate port into the second section of the dosing chamber, such that when said reciprocating portion of the actuation means is moved into the second position the dose of fluid which is forced into the first section of the dosing chamber and which forcibly expands the membrane toward the outlet port into a diastolic position thereby causes the membrane to eject a previous dose of fluid residing in the second section of the dosing chamber out of the outlet channel to the patient.

2. A fluid delivery device as defined in claim 1, wherein the membrane includes an outer perimeter edge and is continuously sealed to the interior walls of the housing along substantially the entire perimeter edge such that the first and second sections of the dosing chamber are divided by the membrane.

3. A fluid delivery device as defined in claim 1, wherein the expanded configuration of the membrane and the elastic memory of the molecular structure of the membrane co-act to contract the membrane toward the inlet port and against the first interior side wall of the housing to a systolic position when the reciprocating portion of the dosing actuation means is moved to the second position.

4. A fluid delivery device as defined in claim 1, wherein the guide channel means and the dosing actuation means collectively comprise:

first channel means disposed to fluidly connect the inlet channel with the inlet port, said first channel means having a diversion port formed therein at a point between the inlet channel and the inlet port;

second channel means disposed to fluidly connect the diversion port with the intermediate port;

first valve means disposed in the first channel means between the inlet channel and the diversion port for alternately blocking and releasing fluid flow within the first channel means when maneuvered into closed and opened positions, respectively;

second valve means disposed in the second channel means between the diversion port and the intermediate port for alternately blocking and releasing fluid flow within the second channel means when maneuvered into closed and opened positions, respectively; and reciprocating actuation means movable into a first position for opening the first valve means and closing the second valve means, and into a second position for closing the first valve means and opening the second valve means, such that a distal section of the first channel means between the diversion port and the inlet port alternately channels fluid in first and second opposing directions in that movement of the reciprocating actuation means into the first position causes said distal section to channel fluid in a first direction toward the inlet port into the first section of the dosing chamber, and movement of the reciprocating actuation means into the second position causes said distal section to channel fluid in a second direction away from the inlet port and toward the diversion port and intermediate port into the second section of the dosing chamber.

5. A fluid delivery device as defined in claim 4, wherein the reciprocating actuation means further comprises:

support means;

first and second valve pins each including a proximal and a distal end, said first and second valve pins being slidably disposed in the support means and being respectively biased toward the first and second valve means and thereby tending to maintain said first and second valve means in closed positions, such that movement of the valve pins into the support means causes the distal ends of said pins to move into contact with their respective valve means to thereby force said valve means into closed positions;

first and second lever means respectively attached at first portions thereof to the support means and being respectively biased at second opposing portions thereof against proximal ends of the first and second valve pins in first switched positions for exerting pressure upon said valve pins to thereby force said first and second valve pins into contact with the first and second valve means;

rigid shaft means including a shaft body and first and second opposing ends, said shaft means being pivotally mounted to the support means at a pivot point thereof, said first opposing end having first and second opposing sides, said second opposing end including first and second rod members extending laterally outward in opposing directions from the shaft body;

first shape memory means secured at one end thereof to the support means and attached at an opposing end thereof to the first side of the first end of the shaft means;

second shape memory means secured at one end thereof to the support means and attached at an opposing end thereof to the second side of the first end of the shaft means;

means for alternately passing electrical current through the first and second shape memory means to thereby alternately cause the first shape memory means and the second shape memory means to contract in alternating tandem, wherein contraction of the first shape memory means causes the shaft means to pivot about its pivot point in one pivotal direction and wherein contraction of the second shape memory means causes the shaft means to pivot about its pivot point in a second pivotal direction, such that the contraction of the first and second shape memory means in alternating tandem causes the first and second rod members to forcibly push the second portions of the first and second lever means away from the support means into second switched positions to thereby mobilize the first and second valve means into open positions and then slide said rod members away from said first and second lever means to release said lever means back into their natural biased positions against the first and second valve pins in alternating tandem.

6. A fluid delivery device as defined in claim 1, wherein the intermediate dosing chamber comprises a lens-shaped concavo-convex chamber such that the first interior side wall comprises a convex wall and the second interior side wall comprises a concave wall, wherein said convex and concave walls are joined together at their perimeters to form an intermediate circumferential section of the dosing chamber, said resilient membrane being sealably attached in an expanded configuration along a circumferential portion thereof to said intermediate circumferential section of the dosing chamber.

7. A fluid delivery device as defined in claim 1 further comprising pressure varying means connected to the pressure means for selectively varying magnitude of the pressure exerted by the pressure means within the reservoir, to thereby vary the rate of transport of the fluid to and from the dosing chamber.

8. A fluid delivery device as defined in claim 4, wherein the reciprocating actuation means further comprises:

shaft means disposed between the first and second valve means, said shaft means including first and second opposing portions and being pivotally anchored at a pivot point thereof;

first and second shape memory means attached to opposite sides of the second opposing portion of the shaft means, said first shape memory means being operable to move the shaft means away from the first valve means and into contact with the second valve means to thereby close said first valve means and open said second valve means, said second shape memory means being operable to move the shaft means away from the second valve means and into contact with the first valve means to thereby close said second valve means and open said first valve means;

means for alternately passing electrical current through the first and second shape memory means to thereby alternately cause the first shape memory means and the second shape memory means to contract in alternating tandem.

9. A fluid delivery device as defined in claim 1, wherein the outlet means includes a distal end portion configured for attachment to an intravenous needle to thereby permit the fluid delivery device to deliver fluid into a vein of the patient.

10. A fluid delivery device as defined in claim 1 wherein said device is portable and miniaturized and configured for attachment to the patient to thereby enable the device to be carried by the patient.

11. A fluid delivery device as defined in claim 10 wherein said device is dimensioned and sized to be swallowable by the patient to thereby enable said device to deliver fluid within an intracorporeal region of the patient.

12. A fluid delivery device as defined in claim 10 further including attachment means for attaching the device to an exterior portion of the patient to thereby enable the device to deliver the fluid to the patient in a topical manner.

13. A fluid delivery device as defined in claim 1 further comprising control means including timing means, said control means being connected to the dosing actuation means for activating and deactivating said dosing actuation means responsive to a timing signal produced by the timing means.

14. A fluid delivery device as defined in claim 1 further comprising control means including sensing means responsive to physiological conditions of the patient, said control means being connected to the dosing actuation means for activating and deactivating said dosing actuation means responsive to an actuation signal produced by the sensing means.

15. A fluid delivery device as defined in claim 5 wherein the first and second valve means comprise resilient membrane material disposed in the first and second channel means, respectively, such that movement of a valve pin into the membrane material causes said membrane material to block fluid flow within the channel means.

16. A fluid delivery device as defined in claim 5, wherein at least one of the first and second opposing sides of the first opposing end of the shaft means includes a finger member formed thereon, and wherein the attachment of shape memory means to said at least one of the first and second opposing sides comprises said shape memory means being looped around said finger member.

* * * * *